United States Patent
Bente et al.

[11] Patent Number: 5,827,481
[45] Date of Patent: Oct. 27, 1998

[54] CARTRIDGE SYSTEM FOR EFFECTING SAMPLE ACQUISITION AND INTRODUCTION

[75] Inventors: H. Bryan Bente, Landenberg; Michael David Glaser, West Grove, both of Pa.

[73] Assignee: Hewlett-Packard Company, Palo Alto, Calif.

[21] Appl. No.: 903,014

[22] Filed: Jul. 31, 1997

[51] Int. Cl.$^6$ .................................................. G01N 35/10
[52] U.S. Cl. ................................ 422/81; 422/63; 422/70; 422/100; 422/103; 436/52; 436/54; 436/161; 436/174; 436/180; 73/23.41; 73/61.55; 73/64.56; 96/105; 96/106; 210/198.2
[58] Field of Search ............................... 422/63, 68.1, 70, 422/81, 100, 102, 103; 436/43, 52, 54, 161, 174, 180; 73/23.41, 51.55, 64.56, 863.12, 864.72, 864.91; 96/105, 106; 210/198.2

[56] References Cited

U.S. PATENT DOCUMENTS

| | | | |
|---|---|---|---|
| 3,881,345 | 5/1975 | Pollock et al. ............................. | 422/70 |
| 4,526,686 | 7/1985 | Sisti et al. . | |
| 4,615,226 | 10/1986 | DiNuzzo et al. . | |
| 5,150,601 | 9/1992 | Simeroth et al. ....................... | 43/23.41 |
| 5,236,668 | 8/1993 | Higdon . | |
| 5,277,871 | 1/1994 | Fujii et al. .................................. | 422/70 |
| 5,462,660 | 10/1995 | Sigleton et al. ...................... | 210/198.2 |
| 5,549,819 | 8/1996 | Nickerson . | |
| 5,734,089 | 3/1998 | Thompson et al. .................... | 73/19.12 |

*Primary Examiner*—Long V. Le
*Attorney, Agent, or Firm*—Mark Z. Dudley

[57] ABSTRACT

A device for performing sample acquisition and introduction of a selectable quantity of the acquired sample to associated device such as an analytical instrument. The preferred embodiment of a the device includes a reservoir for reserving a quantity of sample, a sipper section having a nozzle for inserting an exposed orifice extending therefrom into a sample aggregation, a pump for forcing a quantity of sample from the sample aggregation through the nozzle and into the reservoir, a metering section having a selectably operable motive force unit and a metering unit for withdrawing a sample quantity to be analyzed from the reservoir and for causing the withdrawn sample quantity to be metered into at least one discrete sample quantity of selectable volume, a vaporization section having a vaporizing chamber for receiving the discrete sample quantity and a vaporizer for optionally causing the volatile components of the discrete sample quantity to be volatilized, and an interface which is connected to the vaporization chamber and adapted for insertion into the carrier fluid stream of the instrument. The vaporization chamber may be pneumatically coupled on demand to a carrier fluid stream whereby the metered or volitalized sample components may be rapidly introduced to the carrier fluid stream so as to effect a sample component/ carrier fluid mixture.

10 Claims, 3 Drawing Sheets

CARTRIDGE SYSTEM FOR EFFECTING SAMPLE ACQUISITION AND INTRODUCTION

FIELD OF THE INVENTION

The present invention relates generally to sample analysis systems and, more particularly, to an apparatus and method for optimizing the acquisition of a sample and delivery of the sample to an analytical instrument for subsequent analysis.

BACKGROUND OF THE INVENTION

In analytical chemistry, various analytical techniques have become important tools in the identification of chemical sample components. One useful technique is chromatography. The basic mechanism underlying chromatographic analysis is the separation of a sample mixture into individual components by introducing the sample into a carrier fluid and transporting the resulting mixture through a specially-prepared separation column for subsequent elution as separately detectable components.

Accordingly, various methods and apparatus have been developed to perform the tasks of acquiring a sample (i.e., sample acquisition) and delivery of a controlled amount of the acquired sample to the analytical instrument (i.e., sample introduction).

One approach uses a vaporizing inlet. Liquid samples are typically acquired and introduced to the instrument by using a small volume (e.g., 1–10 $\mu$L) syringe. The syringe is loaded with sample and the syringe needle is placed into the instrument through a septum. The sample is forced into a vaporizing zone so as to be vaporized and mixed with carrier gas, and then swept onto the column. This technique can result in behavior that is not linear with sample injection volume, or that discriminates against certain sample components. These effects lead to quantitative error in the sample analysis. Further, the syringe needle has a significant volume relative to the desired injection volume. Injection into a heated vaporizing region allows any sample remaining in the syringe (typically between 0.5 and 1 $\mu$L) to enter the vaporizing zone and flow into the column. Sample discrimination and quantitative error will result. A so-called "fast" injection reduces this problem but requires the injection to be automated; also, a fast injection causes an undesirable vaporization pressure pulse. Other problems pertinent to the use of a vaporizing inlet include leaks, the presence of septum particles in the vaporizing zone or column, and contaminants from the septum which enter the column and interfere with the analysis. Further, a sample may contain non-volatile components which remain in the inlet and interfere with subsequent analyses. A removable liner can be used in the vaporizing area so that deposits may be removed according to a schedule. However, deposits can accumulate quickly; liner replacement is disruptive and reduces productivity.

Alternatively, the sample may be injected directly into the column itself. Often, however, the injected sample volume is undesirably large for use in a narrow bore capillary columns having an internal diameter of less than 530 micrometers ($\mu$m). Large sample amounts can overload the column and degrade the peak shape and resolution as well as shift the retention time.

Sampling valves can be operated to acquire and then deliver a predetermined quantity of sample into one or more fluid streams in a fluid flow system. The sample is contained in a "loop", such as an attached length of tubing or an etched groove in a valve rotor. The sample is injected by rotation of the valve rotor so that the loop becomes part of the fluid stream. However, there are drawbacks in this approach, such as sample carryover and cross-contamination of samples.

There is accordingly a need for a compact, simple, manually-operable device for acquisition and introduction of a quantity of the acquired sample. The device would be suited for use not only in the laboratory, but more importantly, in a location outside of the laboratory. Such a device would be considered quite portable and would be useful outside of the laboratory for performing process sampling, remote sample analysis, and field monitoring. It would also be desirable and of considerable advantage to provide a device for effecting sample acquisition and introduction that is effective in the field, even if such a new device provided only moderate performance, if it were inexpensive, versatile, and highly portable.

A need also exists to simplify the conventional approach to performing sample acquisition and introduction with respect to a chromatograph, regardless of whether these tasks are performed in the field or in the laboratory, because conventional procedures are expensive, labor-intensive, equipment-intensive, and time-consuming. For example, as the composition of a sample is unknown, the sample may present a bio-hazard to the person acquiring or analyzing the sample. There is accordingly a need for a device for acquiring a sample and introducing a sample to an instrument without exposing the operator or others to sample residue that may be present on the device.

Also, there still remains an unresolved need for a simple and inexpensive apparatus for acquiring a sample and for delivering an ultra small (picoliter or nanoliter) quantity of the acquired sample into a fluid flow. This need is especially apparent in high-resolution chromatography.

SUMMARY OF THE INVENTION

Accordingly, the present invention provides a cartridge system for acquisition of a sample and for introduction of a selectable quantity of the sample to an analytical instrument, whereby the sample acquisition and introduction tasks may be effected safely, easily, and inexpensively, and wherein the introduction is more accurately and reliably performed, to afford improved qualitative and quantitative analysis of the sample.

The present invention provides a method and apparatus for field-portable or in situ performance of at least one of the tasks of sample acquisition and introduction. Sample acquisition may be performed with respect to a sample aggregation present in a variety of forms, circumstances, and locations. The contemplated sample aggregation may be presented in such forms as an effluent, pond, stream, sludge, mound, spray, cloud, foam, and the like, or located in such places as a outdoor field, manufacturing assembly line, industrial process stream, or in such vessels as a vat, gutter, tube, well, seam, crevice, etc.

In particular, the contemplated device is useful for effecting sample acquisition via a manually operated, field-portable device so as to obtain a sample volume in a fashion that allows one to quickly and easily introduce the acquired sample into a field-portable analytical instrument.

In particular, the contemplated device is useful for effecting a volatilization process in a compact unit having a cartridge format, so as to allow automated presentation of a metered sample volume by hand or by automated machinery into: an automated analytical instrument; a portable analytical instrument; a non-portable analytical instrument that may be situated nearby the site of sample acquisition, such as in a vehicle; or an instrument at a location quite distant from the acquisition site, such as in a laboratory.

A preferred embodiment of a system constructed according to our invention includes a system for performing sample acquisition and introduction of a selectable quantity of the acquired sample to associated means such as an analytical instrument. The contemplated system employs a cartridge-shaped device hereinafter described as a sample acquisition and introduction device, or SAID. The preferred embodiment of the SAID includes a reservoir for reserving a quantity of sample, a sipper section having a nozzle for inserting an exposed orifice extending therefrom into a sample aggregation, a pump for forcing a quantity of sample from the sample aggregation through the nozzle and into the reservoir, a metering section having a selectably operable motive force unit and a metering unit, which may optionally be combined in a transport/metering unit, for withdrawing a sample quantity to be analyzed from the reservoir and for causing the withdrawn sample quantity to be metered into at least one discrete sample quantity of selectable volume, and a vaporization section having a vaporizing chamber for receiving the discrete sample quantity and a vaporizer for causing the volatile components of the discrete sample quantity to be volatilized, and inlet and outlet pneumatic connector means and valve means which are connected to the vaporization chamber, wherein the inlet and outlet pneumatic connector means are adapted for inclusion into the carrier fluid stream of the instrument, whereby the vaporization chamber may be pneumatically coupled on demand to the carrier fluid stream, and whereby the volatilized sample components may be rapidly introduced to the carrier fluid stream so as to effect a sample component/carrier fluid mixture.

In the preferred embodiment of a system constructed for carrying out the teachings of this invention, an analytical instrument includes a carrier fluid source for providing a controlled fluid stream of carrier fluid, an interface for receiving the carrier fluid stream and including the vaporization chamber of the SAID so as to provide a carrier fluid/sample component mixture, a separation column connected to the instrument interface for receiving the carrier fluid/sample component mixture and for separating the mixture into at least one component to be detected, and a detector connected to the separation column for detecting the component.

A sample acquisition and introduction method of the present invention includes the steps of: operating the SAID for insertion of the sipper nozzle into a sample aggregation; activating the pump to cause a sample volume to be captured and placed in the reservoir; attaching the SAID to an instrument interface for connecting pneumatic connectors on the SAID to a carrier fluid stream; activating valve element(s) associated with the pneumatic connectors so as to couple the vaporization chamber to the carrier fluid line, such that the vaporization chamber is swept with carrier gas and thereby purged; deactivating the valve element(s) for disconnecting the vaporization chamber from the carrier fluid stream, such that the vaporization chamber contains carrier gas; activating the sample metering section for effecting delivery of a metered portion of the captured sample volume to the vaporization chamber; activating the vaporizer for effecting vaporization of the metered amount into a volatilized portion; activating valve element(s) to direct the carrier fluid into the vaporization chamber for effecting a mixture of carrier fluid and the volatilized portion, thus producing a sample mixture; deactivating the valve element(s) for disconnecting the vaporization chamber from the carrier fluid stream; and optionally purging and venting the vaporization chamber.

In one aspect of the invention, the sipper section includes a fluid nozzle for insertion into an aggregation of sample and for collecting a quantity of sample to the reservoir, which is internally situated, with minimal exposure of the SAID exterior to the aggregation, and with no exposure of the human operator to the sample aggregation. The fluid nozzle may optionally include a nozzle shield that is removable or otherwise actuated for disposal to obviate the continued presence of sample residue on the exterior of the SAID, such that the SAID may thereafter be manipulated by an operator or by automated machinery without concern for exposure to the sample. The nozzle shield may be constructed as an inexpensive, disposable/recyclable, snap-fitting piece. After the sample acquisition is performed, the nozzle shield may be grasped by a gloved hand, or by a bare hand with use of an interposed barrier such as a plastic bag, and removed from the SAID for disposal so as to ensure that such exposure is minimized. Alternatively, the nozzle shield may be ejected by a operation of an ejection means in the SAID or with use of an ejection tool whereby the nozzle shield is directed into a suitable container for subsequent disposal, reclamation, or recycling.

A particular feature of the invention provides an optimized device for producing one or more sample components in a gaseous phase for analysis by a chromatograph. Such samples include, but are not limited to, components that are considered volatile.

Another feature of the invention provides an improved system for interfacing sample mixture to a separation column in a chromatograph, wherein one or both of the sample acquisition and introduction tasks may be effected in a more accurate fashion. As a result, the chromatograph affords improved quantitative analysis of the analyte.

Another feature of the invention provides for accurate metering of an acquired sample into one or more discrete amounts, thus enabling optimization of the sample analysis.

Another feature of the invention provides an improved system for introducing a sample to a separation column in a chromatograph, wherein other sample introduction modes (such as split, splitless, bypass, on-column, programmed temperature vaporization (PTV), or direct injection modes) may nonetheless be accommodated.

Another feature of the invention provides a system that is compact and incorporates miniature or micro-miniature fluid transfer paths, components, and chambers (such as the vaporization chamber). The metered sample is conveyed in transfer paths that exhibit minimal dead volume, so as to minimize the necessary sweep time, the potential interaction of solutes with the active surfaces of the fluid paths, and the tendency for band-broadening.

Another feature of the invention provides a data record medium integrated in the SAID in the form of label strip for handwriting by use of a writing tool, or a machine-readable/writable media strip using electronic, magnetic, optical, or other recording media. Each SAID may optionally include a serial identification code upon manufacture such that each device is unique in its configuration, identity, origin, etc.

Another feature of the invention provides a method and apparatus for automated sample acquisition, and for subsequent automated sample introduction to an analytical system or analytical instrument, and is especially suited for use with a process chemistry analysis.

Another feature of the invention provides a device constructed to function as a lightweight, rugged, compact, field-serviceable, and easily-manipulated unit. It may be constructed as a hand-held device no bigger than a credit card and can be used in the field without reliance upon the typical attributes of a laboratory (such as electrical power, extensive supplies, and a clean working environment). In the field environment, where there can be a need for performing a great number of sample acquisition and introduction tasks in a short time, the contemplated device may be operated in a quick and easy fashion. Because an analytical instrument operator may be working in an adverse or hazardous environment, and may be wearing gloves, a mask, and other protective clothing or apparatus, the contemplated device is constructed to be easily manipulated in such conditions.

The contemplated device employs a design for its construction and configuration such that a quantity of such devices, having been used in acquiring a respective number of samples, may be stacked, collated, or otherwise organized with ease. Later, perhaps in a laboratory, the collection may be arranged for insertion by automated machinery into an analytical instrument for performing a series of respective analyses. Alternatively, one device may easily be retrieved from a group of same that have been collected in a less-than-orderly fashion into a basket, bag, rack, or the like for performing an analysis of the extracted analyte(s) in an analytical instrument. Any or all of the devices may be reserved for archival purposes until selected for disposal or recycling.

In another feature of the invention, the contemplated device has the ability to acquire differing quantities, forms, and types of samples, and is useable without major modifications when such a variety of samples or sample aggregations is presented.

In another feature of the invention, a SAID is amenable to production in large numbers at lost cost in one or more highly standardized configurations, thus making the contemplated SAID ideal for facilitating archival, chain-of-custody, and other evidentiary and record-keeping purposes.

Many of the foregoing attributes are especially beneficial when the SAID is used for the type of repetitive operations that are typically performed in a process quality control or manufacturing quality control operation, on-line or off-line monitoring operation, or field monitoring operation. Whereas a SAID is highly useful when deployed in the field, it nonetheless is amenable to use with any integrated analytical instrument, whether that instrument is also field-portable, located in a vehicle, located in a permanent operation such as a industrial process line, or maintained in a laboratory.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention. The description of components of like nomenclature and reference numerals in the following are intended to be equivalent. Single lines in the illustrations are meant to represent electronic signal lines; bold lines are meant to represent fluid-bearing lines.

DETAILED DESCRIPTION OF THE PREFERRED EMBODIMENTS

The apparatus and methods of the present invention may be employed to improve the sample acquisition, preparation, and introduction of a sample to a separation column in an analytical chromatographic system. Gases are the preferred carrier fluids according to the practice of the present invention; therefore, the following description of the invention is directed for explanatory purposes to a gas chromatographic analytical system. Further, the description herein is directed to certain pneumatic characteristics of fluids. However, as used herein, the term "fluid" should not be considered as being limited to gases but may also include liquids, vapors, fluidized aggregations such as fine particles, and the like.

The carrier fluid may comprise one or more components (such as hydrogen, nitrogen, argon-methane, or helium) depending upon the particular chromatographic separation to be performed. However, it should be understood that the teachings herein are applicable to other carrier fluids.

Further, the present invention will find useful application in a variety of fluid handling systems that benefit from the delivery of an ultra small volume of a sample into a fluid flow. Such systems are commonly employed in a wide variety of applications, such as sample purification, chemical analysis, clinical assay, industrial processing, water purification, reagent dispensing, manual and automated solid phase extraction, supercritical fluid extraction, stopped-flow spectrophotometry, clinical analysis, automated protein or nucleic acid sequencing, pharmaceutical development, and solid phase protein or nucleic acid synthesis. Further examples that are particularly benefited by an application of the present invention include liquid chromatography, capillary electrophoresis chromatography, and flow-injection analysis.

A constituent component of interest in a sample presented in a solid, fluid, or gaseous form may be captured by performing sample acquisition as will be described below. Alternatively, a constituent component of interest in a solid sample may first be obtained by solvation, whereby application of a solvent fluid to the sample causes constituent components to be dissolved in the solvent so as to create a solvent mixture, followed by acquisition of the solvent mixture.

Figure 1:
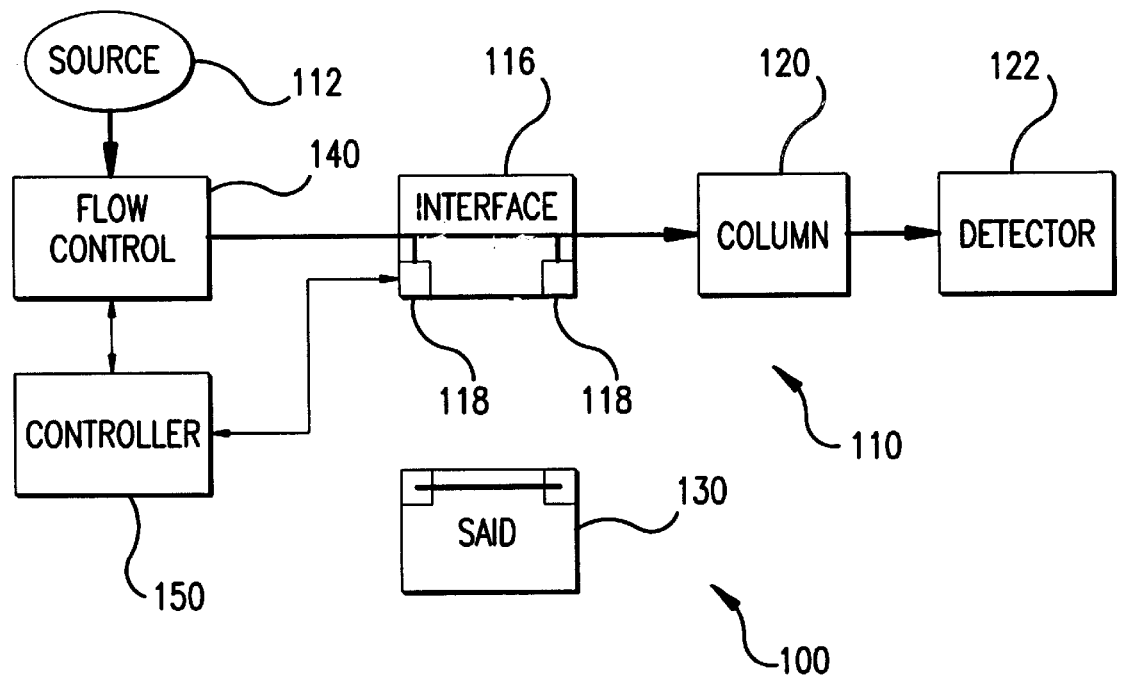
FIG. 1 is a simplified representation of an embodiment of an analytical instrument constructed according to the present invention.
Figure 2:
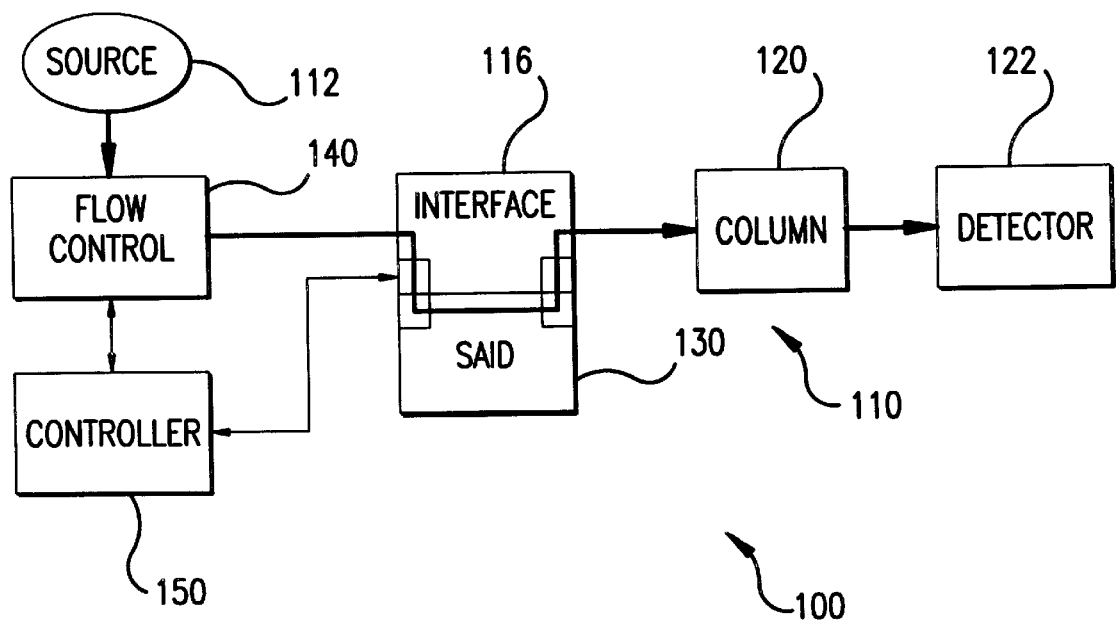
FIG. 2 is a simplified schematic representation of the analytical instrument of FIG. 1 wherein a preferred embodiment of a SAID may constructed according to the present invention and docked to the instrument.

As shown in FIGS. 1–2, a preferred embodiments of an analytical instrument system 100 includes a chromatograph 110 and a novel sample acquisition and introduction device (SAID) 130 that are constructed according to the present invention.

The illustrated system 100 may be constructed to enable, at a minimum, sample introduction when configured in a novel sample introduction mode as will be described herein, but preferably other suitable injection modes are operable at points elsewhere in the instrument system 100 as known in the art.

FIG. 1 shows an exemplary system 100 having the flow path of a carrier gas flow from a supply 112 passed through a flow controller module 140 to an inlet interface 116 having pneumatic connectors 118. The flow of the carrier gas entering the inlet interface 116 is controlled by the flow controller module 140 in response to an appropriate control signal provided by a controller 150. By use of known make-or-break valve means in the pneumatic connectors 118, the carrier gas flow is selectively directed through either the inlet interface 116 and on to a separation column 120, or to the SAID 130 when the SAID 130 is present in the interface 116, or both.

Hence, as shown in FIG. 2, the system 100 may be operated in a sample introduction mode wherein a metered quantity, or a metered and vaporized quantity, of sample is introduced into the carrier gas flow by the SAID 130 whereby the sample/carrier gas mixture is directed into the separation column 120. Accordingly, the illustrated SAID 130 is capable of performing either sample metering or metered sample vaporization, or both.

Typically, the temperature of the column 120 is controlled according to known techniques so that the sample will separate into its components. As the carrier gas (containing the sample) exits the column 120, the presence of one or more sample constituent components is detected by a detector 122.

As shown in FIG. 2, insertion (i.e., "docking") of the SAID 130 into the interface 116 places the system 100 in a sample introduction mode. Docking of the SAID 130 then causes a carrier fluid stream from the carrier fluid source 112 to be available to the SAID 130 from the carrier fluid flow controller 140. As will be described below, the carrier fluid stream may be selected to pass through a vaporization chamber in the SAID 130 to purge the chamber and then pass to the column 120. At a selectable point in time, the vaporization chamber is closed and a metered amount of sample is directed into the vaporization chamber. In an optional step depending upon the characteristics of the sample, the metered quantity of sample is vaporized. The stream of the carrier fluid stream is then re-directed through the vaporization chamber to provide a sample/carrier fluid mixture. The sample/carrier fluid mixture is then output from the SAID 130 and is directed as a column fluid stream to the separation column 120 and then to a detector 122.

The temperature of the column 120 is controlled according to known techniques so that the sample components introduced by the SAID 130 will separate into eluted components at the outlet of the column 120. As the carrier gas (containing the eluted sample components) exits the column 120, the presence of one or more sample constituent components is detected by the detector 122.

When interconnected in the sample introduction mode, the preferred embodiments of the inlet interface 116, pneumatic connectors 118, and SAID 130 are constructed (using suitable fittings and fluid bearing channels) to employ a commonly-shared, but minimal-volume, fluid path for passing the carrier fluid stream through the vaporization chamber. The fluid bearing channels that define such an internal volume are preferably narrow-bore (i.e., low volume) channels having interior surfaces formed of a chemically inert material. One preferred amount of the internal volume for the combined fluid path is approximately 25 microliters or less.

The illustrated embodiment includes electronic control, power, and data lines connected from a system controller 150 through the interface 118 to the SAID 130 when it is docked in the interface 118.

The controller 150 preferably includes power, data acquisition, memory, computation, and other circuitry suited for initiating and controlling the various functions relative to operation of the system 100 as described herein, and software and/or firmware pertinent to carrying out the functions and operations indicated herein, and in particular the generation, storage, retrieval, editing, and the like of information recorded in the SAID 130. The preferred embodiment of the controller 150 is constructed to operate as a table-driven control system wherein the configuration and operation of the system 100, and particularly the control of the gas streams operative in the aforementioned sample introduction mode, may be controlled by the EPC 140 in conjunction with the controller 150.

An operator may perform data entry and retrieval to and from the SAID 130 and control table editing by way of a suitable apparatus connectable to the controller 150. Data retrieved or entered into the SAID 130 may include a variety of information about the system 100, including the identity and other information relevant to the sample contained in the SAID 130. For example, sample acquisition information prerecorded in the SAID 130 is contemplated as being obtained or updated prior to or during the sample introduction mode.

Figure 3:
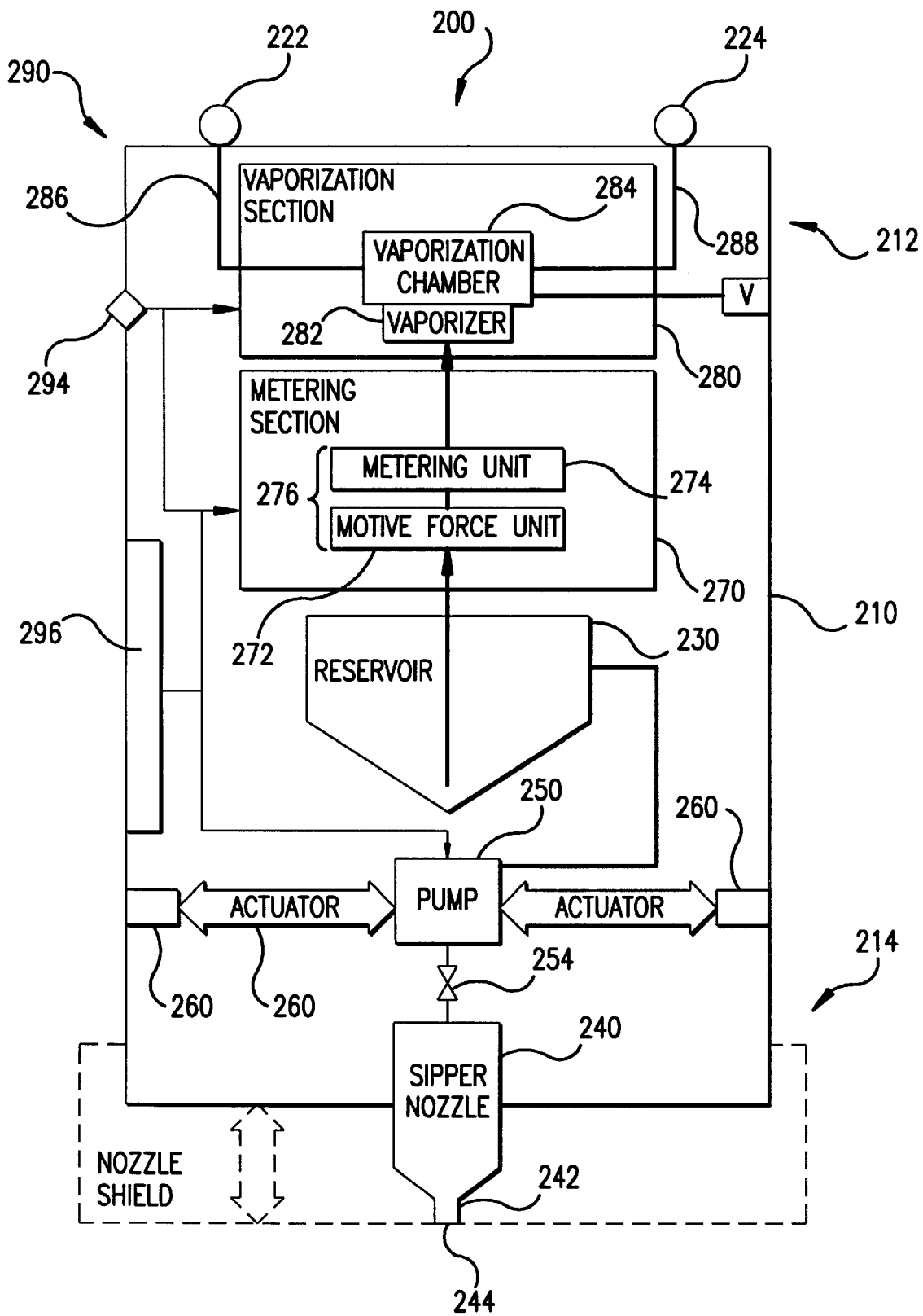
FIG. 3 is a simplified schematic representation of the SAID of FIG. 2.
Figure 4:
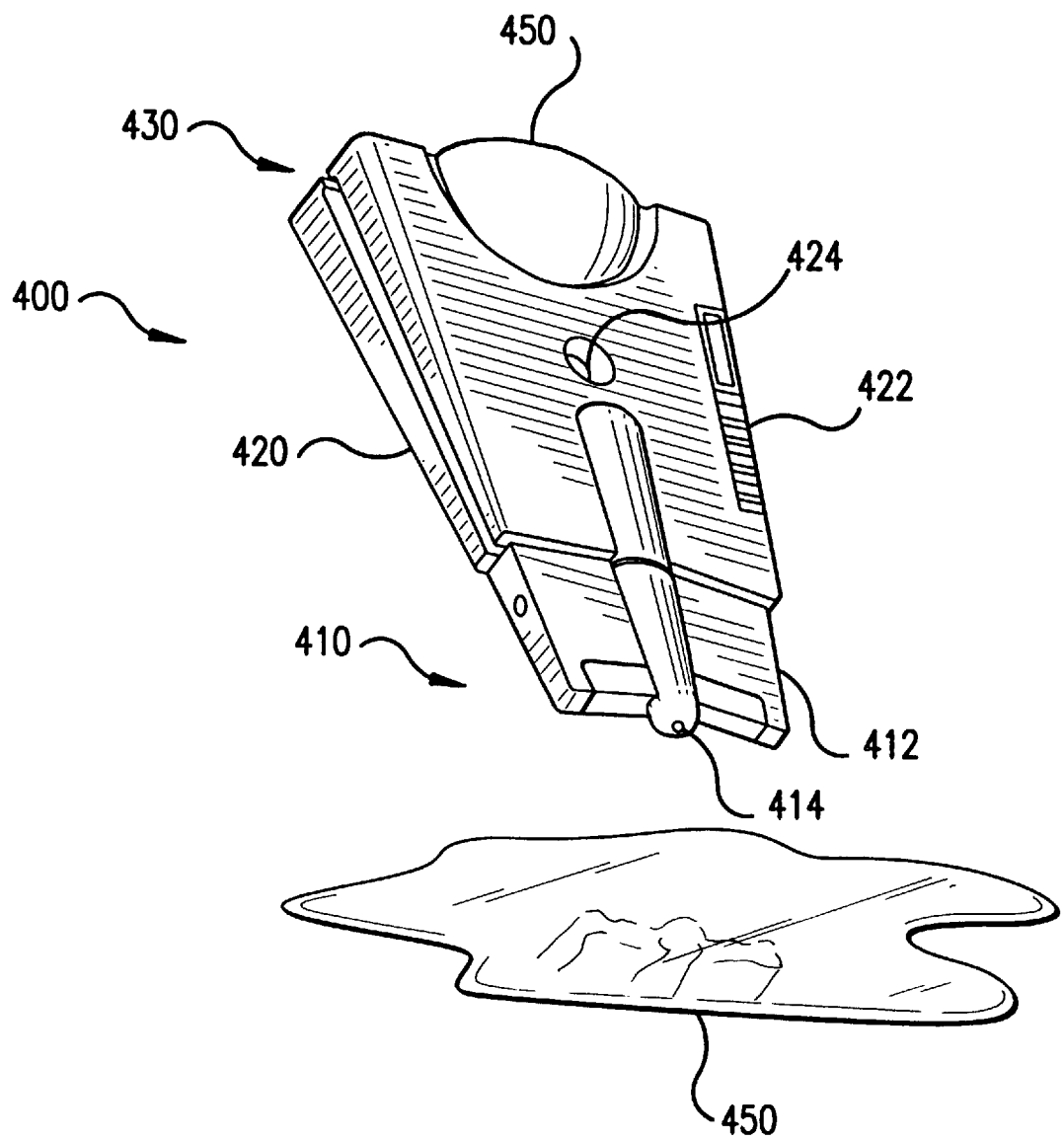
FIG. 4 is a simplified side perspective illustration of another embodiment of a SAID constructed according to the present invention and illustrated in a sample acquisition mode of operation.

As illustrated in FIG. 3, a preferred embodiment of the SAID 200 may be understood to include a compact and lightweight housing 210 having an interface end 212 and a nozzle end 214. Inlet and outlet pneumatic connectors 222, 224 are attached to the interface end of the housing and operate as mechanical and pneumatic complements of respective ones of the pneumatic connectors 118 on the inlet interface 116. A reservoir 230 is provided within the housing for reserving a quantity of sample. A sipper section 240, located at the nozzle end 214, includes a nozzle 242 having an exposed orifice 244 extending therefrom, useful for entry into a sample aggregation. A pump 250 is provided for forcing a controllable quantity of sample from the sample aggregation through the nozzle and into the reservoir 230. An optional actuator 260 may be provided for manual operation of the pump.

In an alternative embodiment, the reservoir 230 is provided in a manufacturing step with a negative pressure and then sealed at the pump 250, and the pump 250 is configured to operate as a valve on the inlet line to the reservoir 230. Later, when deployed for sample acquisition, the SAID 200 may then be operated to force a sample quantity into the reservoir 230 by manipulation of the actuators 260 to thereby cause the seal in the pump 250 to be altered, thus causing the negative pressure in the reservoir to draw a sample quantity through the nozzle 240 and pump 250 into the interior of the reservoir 230.

A metering section 270 having a selectably operable motive force unit 272 and a metering unit 274, which are optionally combined as a transport/metering unit 276, is provided for drawing a sample quantity from the reservoir and for causing the withdrawn sample quantity to be metered (i.e., measured or divided) into at least one discrete sample quantity of precisely selectable volume.

The metered amount is then deposited in a vaporization section 280.that includes a vaporizing chamber 282, a vaporizer 282, and inlet and outlet fluid paths 286, 288 coupled respectively to the inlet and outlet pneumatic connectors 222, 224. The vaporizer 284 may be integrated in the vaporization chamber for vaporizing the sample quantity held therein, or may be interposed in the fluid path between the vaporization chamber 284 and the metering unit 274 for vaporizing the discrete sample quantity en route to the vaporization chamber 284.

An interface 290 includes the inlet and outlet pneumatic connectors 222, 224 and an electronic signal and power connector 294, the latter being provided for coupling control, data, and power lines to complementary electrical connector(s) in the inlet interface 116. The inlet and outlet pneumatic connectors 222, 224 are preferably coupled to the vaporization chamber 284 via fluid paths 286, 288 having integral microminiature valve means such that the vaporization chamber 284 may be sealed or opened to fluid flow in the paths on demand. The inlet and outlet pneumatic connectors 222, 224 are preferably adapted for insertion into the inlet interface 116 whereby the force of such insertion secures fluid-tight pneumatic coupling of the vaporization chamber 284, fluid paths 286, 288 to the pneumatic connectors 118. Concurrent coupling of the electrical connector 294 to a corresponding connector in the inlet interface 116 is effected in this fashion as well.

Activation of certain ones of the aforementioned components, such as vaporization section 280, may be effected according to signals provided to the electrical connector 294. It is contemplated such that the vaporization chamber 284 may be selectively (on demand) coupled to the carrier fluid stream in the inlet interface 116. Accordingly, the volatilized sample components may be rapidly introduced to the carrier fluid stream at a selectable point in time so as to effect a sample component/carrier fluid mixture.

A strip 296 of data recording media is provided for recording indicia relevant to the sample and to the SAID 200 is provided at the housing exterior. The strip 296 may be provided in the form of a scribable or pen- or pencil-receptive surface for handwritten data, or the strip may include electrically-reactive devices such as a simple resistor array and is accordingly coupled to the electrical connector.

Preferred embodiments of the strip 296 include a pressure-sensitive switch array, semiconductor device array, magnetic strip, optical bar code strip, radio-frequency resonant or reactive circuit, and the like.

Preferred embodiments of the pump 250 provide suction at the sipper nozzle for suctioning a quantity of sample and delivering the captured amount to the reservoir 230. Preferred embodiments of the pump 250 include: a resilient bladder having a flow restriction that may be activated in concert with a check valve 254 by use of finger pressure applied to the actuators 260, a transducer operable by thermal, optical, piezoelectric, electrophoretic, magneto restrictive, or electrorestrictive principles for effecting transport of the sample quantity, or a micromachined pump. Any of the foregoing are representative of a variety of known miniature or microminiature means for propelling the sample quantity in a desired direction within a fluid conduit.

Preferred embodiments of the reservoir 230 include a low volume (e.g., 1 to 1000 microliters) cavity integrated in the housing 210 and lined with an inert coating so as to be unaffected by the presence of a reserved quantity of sample. The reservoir 230 may optionally include a baffled structure, or include a porous structure, for preventing gross displacement of the reserved sample quantity within the confines of the reservoir when the SAID is tilted, jarred, etc.

Preferred embodiments of the motive force unit 272 include a transducer operable by thermal, optical, piezoelectric, electrophoretic, magneto restrictive, or electrorestrictive principles for effecting transport of the sample quantity, or a micromachined pump. Any of the foregoing are representative of a variety of known miniature or microminiature means for propelling the sample quantity in a desired direction within a fluid conduit.

Preferred embodiments of the metering unit 274 include a laser or mechanically-machined valve orifice; a micromachined valve orifice provided in a substrate such as silicon; an etched valve orifice provided in a planar semiconductor substrate, and the like.

Preferred embodiments of the vaporizer 282 include means for causing the volatile components of the discrete sample quantity to be volatilized on demand according to an application of thermal, electrical, mechanical, or other similarly nebulizing or vaporizing action to the metered sample present in the vaporization chamber. For example, the vaporizer may include a heating means in the form of a miniature resistor or Peltier heater.

As shown in FIG. 4, another preferred embodiment of a SAID may be constructed in the form of an inexpensive but robust single-use cartridge 400 having a size and shape comparable to a credit card. The illustrated cartridge 400 includes a nozzle end 410 including a detachable nozzle shield 412 that includes a sipper port 414. The body 420 includes an interface end 430, a data recording strip 422, and a fill window 424 for indicating the relative extent of the sample fluid quantity held within an internal reservoir (not shown but comparable to the reservoir 230 of FIG. 3). The sipper port 414 is configured to allow the cartridge 400 to be grasped between thumb and fingers at the interface end 430 while dipping the sipper port 414 into a sample aggregation 450. A resilient squeeze bulb 440 functions in concert with an internal pump (not shown but comparable to the pump 250 of FIG. 3) that is coupled to the reservoir. The bulb 440 may be manipulated while the sipper port 414 is submerged in the sample aggregation so as to induce a negative pressure in the reservoir and thereby draw a quantity of sample into the reservoir. After the sample acquisition is accomplished, the acquired sample is retained in the reservoir by operation of a check valve (not shown but comparable to the check valve 254 of FIG. 3). The nozzle shield 412 may then be detached from the body 420 and discarded or recycled, thus preventing any contact with the sample or sample residue during subsequent handling of the SAID 400.

Certain ones of the foregoing components described as being miniature or microminiature are contemplated as being fabricated by techniques developed in the arts of micromachining, semiconductor fabrication, and micro-electro-mechanical systems (MEMS) to radically reduce the size and format of the described components. Further, it is contemplated that the components described herein with reference to the motive force unit, pump, and vaporizer may be constructed as devices that operate on the conversion of an applied power into an actuation force for moving a movable member, and in particular as thermally-actuated devices that operate at an elevated temperature. Examples are microactuators that are driven by forces developed in a process of gas or liquid expansion/contraction, gas or liquid phase change, or according to changes in bi-morph, bi-metallic, or shape-memory materials. See, for example, U.S. Pat. Nos. 3,538,744 (Karasek); 4,824,073 (Zdeblick); 4,905,497 (Shindo); 4,935,040 (Goedert), 4,474,889 (Terry et al.), 5,333,831 (Barth et al.); and 5,058,856 (Gordon et al.), the contents of which are incorporated herein by reference.

What is claimed is:

1. A device for performing sample acquisition and introduction of a selectable quantity of an acquired sample to a carrier fluid stream in an analytical instrument, comprising:

a reservoir for reserving a quantity of the sample;

a sipper section having a nozzle for inserting an exposed orifice extending therefrom into the sample;

a pump for forcing the quantity of the sample through the nozzle and into the reservoir;

a metering section having a selectably operable motive force unit and a metering unit, for withdrawing a sample quantity to be analyzed from the reservoir and for causing the withdrawn sample quantity to be metered into at least one discrete sample quantity of selectable volume;

a vaporization section having a vaporizing chamber for receiving the discrete sample quantity; and a pneumatic connector which is connected to the vaporization chamber and adapted for insertion into the carrier fluid stream of the instrument, whereby the vaporization chamber being pneumatically coupled on demand to the carrier fluid stream whereby the discrete sample components are introduced to the carrier fluid stream so as to effect a sample component/carrier fluid mixture.

2. The device of claim 1, further comprising a vaporizer operatively connected to the vaporization chamber for causing the volatile components of the discrete sample quantity to be volatilized in the vaporization chamber and whereby the discrete sample components are introduced to the carrier fluid stream.

3. The device of claim 1, wherein the sipper section includes a fluid nozzle operatively connected to the nozzle for insertion into an aggregation of the sample.

4. The device of claim 1, wherein the nozzle is present at a nozzle end of the device and the nozzle includes a nozzle shield that is removable from the device.

5. The device of claim 1, wherein the nozzle shield may be removed by operation of an ejection means.

6. The device of claim 1, wherein the metering section provides for accurate metering of an acquired sample into plural discrete amounts.

7. The device of claim 1, wherein the sample is conveyed in a combination of fluid transfer paths, components, and chambers of micro-miniature size that exhibit minimal dead volume.

8. The device of claim 1, further comprising a strip of data recording media.

9. An analytical instrument for performing an analysis of a sample, comprising:

a carrier fluid source in the analytical instrument for providing a controlled fluid stream of carrier fluid;

a sample acquisition and introduction device for performing sample acquisition and introduction of a selectable quantity of an acquired sample in the carrier fluid stream, including:

a reservoir for reserving a quantity of the sample;

a sipper section having a nozzle for inserting an exposed orifice extending therefrom into the sample;

a pump for forcing the quantity of the sample through the nozzle and into the reservoir;

a metering section having a selectably operable motive force unit and a metering unit, for withdrawing a sample quantity to be analyzed from the reservoir and for causing the withdrawn sample quantity to be metered into at least one discrete sample quantity of selectable volume;

a vaporization section having a vaporizing chamber for receiving the discrete sample quantity; and a pneumatic connector which is connected to the vaporization chamber and adapted for insertion into the carrier fluid stream of the instrument, whereby the vaporization chamber being pneumatically coupled on demand to the carrier fluid stream, and whereby the discrete sample quantity is introduced to the carrier fluid stream so as to effect a sample/carrier fluid mixture; and an interface for receiving the carrier fluid stream and the pneumatic connector for coupling the vaporization chamber to the carrier fluid stream so as to provide the sample/carrier fluid mixture.

10. The instrument of claim 9, further comprising a separation column connected to the instrument for receiving the sample/carrier fluid mixture and for separating the mixture into at least one sample component to be detected, and a detector connected to the separation column for detecting the sample component.

* * * * *